United States Patent [19]

Lommi et al.

[11] Patent Number: 5,635,368
[45] Date of Patent: Jun. 3, 1997

[54] BIOREACTOR WITH IMMOBILIZED LACTIC ACID BACTERIA AND THE USE THEREOF

[75] Inventors: Heikki Lommi, Kantvik, Finland; Wilhelmus J. P. M. Swinkels, Beek en Donk, Netherlands; Timo T. Viljava, Kantvik; Roger C. Hammond, Espoo, both of Finland

[73] Assignee: Cultor Ltd., Helsinki, Finland

[21] Appl. No.: 157,759

[22] Filed: Nov. 24, 1993

[30] Foreign Application Priority Data

Nov. 25, 1992 [DE] Germany .......................... 42 39 612.3

[51] Int. Cl.⁶ .............................. C12P 1/00; C12M 1/00
[52] U.S. Cl. .................... 435/41; 435/139; 435/170; 435/179; 435/252.9; 435/299.1
[58] Field of Search ........................ 435/41, 103, 139, 435/140, 141, 174, 176, 177, 178, 179, 180, 183, 288, 299, 310, 813, 853–857, 170, 252.9, 289.1, 294.1, 299.1; 426/7, 11, 12, 18, 34, 43

[56] References Cited

U.S. PATENT DOCUMENTS

| | | | |
|---|---|---|---|
| 4,090,022 | 5/1978 | Tsao et al. | 435/179 |
| 4,355,117 | 10/1982 | Antrim et al. | 435/179 |
| 4,794,080 | 12/1988 | Mays et al. | 435/853 |
| 4,814,273 | 3/1989 | Brumm et al. | 435/177 |
| 4,867,992 | 9/1989 | Boniello et al. | 426/45 |
| 4,929,452 | 5/1990 | Hamdy | 426/11 |
| 4,942,032 | 7/1990 | Vandenbergh et al. | 435/853 |
| 4,970,153 | 11/1990 | Kobashi et al. | 435/853 |
| 5,037,749 | 8/1991 | Findlay | 435/176 |
| 5,075,226 | 12/1991 | Kaneko et al. | 435/853 |
| 5,079,011 | 1/1992 | Lommi et al. | 435/179 |

FOREIGN PATENT DOCUMENTS

| | | |
|---|---|---|
| 0111885 | 6/1984 | European Pat. Off. . |
| 0 186 125 | 7/1986 | European Pat. Off. . |
| 91/0128664 | 4/1991 | Japan . |
| 2085449 | 4/1982 | United Kingdom . |
| 2178447 | 2/1987 | United Kingdom . |
| WO92/03533 | 3/1992 | WIPO . |

OTHER PUBLICATIONS

Champagne et al. "Growth of yeast contaminants in an immobilized lactic acid bacteria system." Letters in Applied Microbiology, vol. 8 (1989). pp. 207–210 1989.

"Contamination of Immobilized Yeast Bioreactors", by J. Kronlof & A. Haikara, *Journal of the Institute of Brewing*, vol. 97, pp. 375–380, London, Oct. 1991.

*Primary Examiner*—William H. Beisner
*Attorney, Agent, or Firm*—Kenyon & Kenyon

[57] ABSTRACT

The invention relates to a bioreactor with immobilized lactic acid bacteria which is characterized in that the bacteria are fixed on the surface of a substantially non-compressible carrier which is composed of a continuous, porous matrix or of dimpled or reticular porous particles, the matrix or the particles having a structure of a loosely associated plurality of microparticles or microfibers which are bound together chemically, adhesively or mechanically at least at some contact points between the individual microparticles or microfibers. Preferably the microparticles or microfibers comprise or consist of a material, preferably a resin, having anion exchanger capability. A preferred embodiment of the carrier includes DEAE-cellulose, the microparticles and microfibers being agglomerated with polystyrene.

22 Claims, No Drawings

BIOREACTOR WITH IMMOBILIZED LACTIC ACID BACTERIA AND THE USE THEREOF

The invention relates to a bioreactor with immobilized lactic acid bacteria and the use thereof.

Fermentation processes were carried out for a long time with the aid of free growing bacteria cultures. It has only recently been recognized that the use of immobilized bacteria could be an advantage. Immobilized bacteria make use in continuous processes possible, contrary to the free bacteria, the bacteria being retained in the bioreactor. The processes with immobilized bacteria make a high concentration of the bacteria possible so that in comparison to free, growing bacteria, greater reaction speeds are achieved and, therefore, smaller dimensioned plants are possible or the duration of the processes can be considerably shortened.

Lactic acid bacteria and products derived from them are widely used in the manufacture of food. The immobilisation of various lactic acid bacteria is also known. A detailed report on the use of immobilized lactic acid producing bacteria in fermentation processes is given by Marc R. Smith and Jan A.M. DuPont, Institut for Industrial Microbiology, Division for Food Science, Agricultural University, PO Box 8129, 6700 EV Wageningen, in their article "The applications of immobilized lactic acid bacteria in fermentation processes".

In this, the immobilisation is effected with various trapping or encapsulating techniques. For example, agar, gelatine or alginate are used in order to involve the bacteria in a gelling process. Cellulose acetate or polystyrene are used in order to achieve the trapping of the bacteria by means of solvent precipitation. Additionally, epoxy resins and polyurethane or polyacrylamide are used in order to achieve the trapping through polycondensation or polymerisation. However, the above mentioned carrier materials result in considerable disadvantages in their transformation to the industrial scale.

Thus, for example, the above mentioned carrier materials are soft and generate unnecessary pressure losses in packed bed reactors at high flow rates or in the use of large units. Additionally, the immobilisation must be carried out separately when the bacteria are fixed in the carrier materials, i.e. the fixing step itself cannot be carried out in the reactor in which the lactic acid production is to later ensue. Finally, in the case of contamination of the carrier or disruption of the process in the reactor for other reasons, a reuse of the carrier materials is impossible. It is also a considerable disadvantage that, in the production of lactic acid by means of fixing the bacteria within the matrix, the reaction rates are limited by diffusion processes.

It is the object of the invention to provide a bioreactor with immobilized lactic acid bacteria which can overcome the above mentioned disadvantages and with which it is possible to realize a process which can be carried out technically and economically on an industrial scale.

The object above is solved by means of a bioreactor with immobilized lactic acid bacteria which is characterized in that the bacteria are fixed on the surface of a substantially noncompressible carrier composed of a continuously porous matrix or of reticular porous or dimpled particles, the matrix or the particles having a structure of a loosely associated plurality of microparticles or microfibers which are chemically, adhesively or mechanically joined to one another at least at some contact points between the individual microparticles or microfibers. Preferably the microparticles or microfibers comprise or consist of a material, advantageously a resin, with anion exchanger capability.

In a preferred embodiment, the carrier comprises cellulose or rayon or their derivatives. These derivatives may be chemically modified in order to provide the anion exchange properties. Preferably, the microparticles or microfibers are agglomerated with one another, e.g. by means of a hydrophobic polymer which exercises the function of an adhesive.

In accordance with a particularly advantageous embodiment, the resin material of the carrier is diethylaminoethylene-modified cellulose (DEAE-cellulose) in accordance with U.S. Pat. No. 4,355,117, the microparticles or microfibers being agglomerated, preferably with polystyrene.

In the production of the above mentioned, preferred carrier, an agglomerate of cellulose is preferably first produced with the hydrophobic polymer, which is then derivatized in an aqueous suspension of the agglomerate under alkaline conditions with the formation of anion exchanger properties. In this case, the agglomerate can be produced by compounding the cellulose with the hydrophobic polymer heated to the plastic condition. A further possibility consists in effecting the agglomerisation by producing a solution of the hydrophobic polymer in an organic solvent and incorporating the cellulose in this.

Suitable as agglomerating substances are, in addition to polystyrene as the preferred polymer, also melamine-formaldehyde resin or an epoxy resin.

A detailed description of the production of agglomerated, fibrous ion exchanging cellulose-composite bodies can be found in the German Patent DE-31 30 178 C2.

A further embodiment of the carrier material contains porous, sintered glass or ceramic materials.

The term "lactic acid bacteria", as used in this invention, encompasses the genera Aerococcus, Carnobacterium, Enterococcus, Erysipelothrix, Gemella, Globicatella, Lactobacillus, Lactococcus, Leuconostoc, Pediococcus, Streptococcus, Tetragenococcus and Vagococcus. These genera are generally characterized in that bacteria belonging to them possess, or originally possessed in their wild-type form, the capacity to produce lactic acid and other specific products.

Homofermentive bacteria such as *Lactobacillus delbrückii*, *Lactobacillus bulgaricus* or *Lactobacillus leichmanii* may be used for the large scale production of lactic acid. *Lactobacillus amylovorus*, *Lactobacillus plantarum* and *Lactobacillus helveticus* may be used for the acidification of beer with lactic acid. Heterofermentative bacteria such as *Lactobacillus brevis*, *Lactobacillus buchneri* or *Lactobacillus mesenteroides* are used for the production of foodstuffs containing lactic acid.

The substrates in which the above mentioned bacteria produce lactic acid by fermentation include compounds consisting of hexoses or compounds which are easily divided into hexoses. These raw materials are present in the substrates to be treated in the bioreactor and include, for example, sugar molasses, sugar cane juice, rice starch, whey, sulphite liquor, potato starch.

In accordance with a preferred embodiment of the bioreactor, the loading capacity, ie. the number of cells per gramme of dry carrier lies in the range of $10_8$ to $10_{12}$. Here one must take care that the loading capacity is set such that a sufficient quantity of lactic acid is produced for the respectively intended purpose. Further factors which are responsible for the quantity of produced lactic acid are also temperature and the flow velocity through the reactor. Furthermore, in the treatment of the substrate in the bioreactor, air is preferably kept away in order to prevent oxidation processes and, therefore, yield losses. The process conditions in the bioreactor are in all cases to be adjusted such that conditions are obtained which do not lead to a dying out of the lactic acid bacteria.

According to a preferred embodiment of the present invention the bioreactor comprises a device allowing the contact of the loaded carrier with a fluid to be reacted. Advantageously the device is selected from among a stirred tank reactor, basket reactor, fluidized bed reactor, packed bed reactor and filter reactor. The bioreactor may also represent a device that is a column or a plurality of columns, advantageously in parallel. In the column(s) the substrate to be treated preferably flows in the direction of gravity.

A further favourable embodiment of the bioreactor also comprises in addition to the device a container for hydrating the dry carrier material ahead of the pumps in the bioreactor, a container with sterilizing fluid for sterilizing the carrier in the bioreactor, a container with neutralizing fluid for neutralizing the carrier after the sterilisation, a container with bacteria suspension for pumping into the bioreactor and fixing on the surface of the carrier, a container with the substrate to be treated, optionally a post-treatment container in which the outflow from the bioreactor is after-reacted, and a container for the storage of the product.

The bioreactor can also include pressure releasing valves and means for separating carbon dioxide.

In the frame of the present invention the bioreactor can be used for the making of products resulting from the metabolism of lactic acid bacteria and for modifying the composition of the feedstream.

According to a particular embodiment the bioreactor is applied in the production of lactic acid, preferably L(+) lactic acid.

With the selection of specific lactic acid bacteria the inventive bioreactor can be used to produce further compounds in addition to or as an alternative to lactic acid. Thereby the production of bacteriocins such as nisin being useful for food preservation can be mentioned. It is also possible to produce specific flavour compounds such as diacetyl, ethanol, propanol, isobutanol, pentanals and hexanals. The inventive bioreactor can also be used to produce specific extracellular enzymes, such as lipase, or polymers, such as dextran, or other organic acids in addition to lactic acid. Furthermore, it is also possible to remove urea from the feedstream by the use of specific cell-bound urease enzymes in the reactor.

A further preferred application of the bioreactor is found in the production of lactic acid in flowable and pumpable food products such as milk or fruit juices.

Finally, the inventive bioreactor can also be advantageously used to acidify beverages such as, for example, juices, lemonades, beer, wine.

The advantages of the inventive bioreactor initially consist in that too high a pressure in the bioreactor itself can be prevented by means of the substantially non-compressible carrier. Furthermore, the claimed bioreactor differs from the prior art in that the bacteria are fixed at the surface of the specifically used carrier and not within the matrix. Therefore, no diffusion barriers occur and, on account of the high bacteria concentration on the surface, perceivably higher reaction rates and, therefore, shorter reaction times and a better utilisation of the substrate can be achieved. The fixing of the bacteria at the surface furthermore causes the effect that the carrier can be regenerated and reused.

The bioreactor according to the invention includes a high capacity and a high flexibility with regard to the manufacture of products resulting from the metabolism of lactic acid bacteria, and in particular, lactic acid. The bioreactor can be kept for several weeks under stand-by conditions and can be started up very easily. The processes in the bioreactor can be performed completely automatically and in a closed system, so that a good biological condition is obtained with no contamination. The inventive bioreactor enables a compact installation and the saving of energy and costs.

In the following, the invention is described in more detail by means of examples, which should not be understood to have a limiting effect.

EXAMPLE 1

Production of a carrier

Granular derivatized cellulose was manufactured according to U.S. Pat. No. 4,355,117 as follows.

25 parts of fibrous cellulose was mixed with 25 parts of titanium dioxide and the mixture was compounded with 50 parts of food-grade high-impact polystyrene using a twin-screw extruder. The extrudate was cooled in water, and sieved to a particle size of 0.35–0.85 mm.

The sieved granular agglomerated cellulose particles were derivatized to form DEAE cellulose as described in the U.S. Patent above.

EXAMPLE 2:

Hydration, sterilisation, loading of the carrier and immobilisation Of the bacteria on the carrier 10 g of the granular DEAE-cellulose produced in example 1 was reduced to a slurry in distilled water and soaked for 5 hours with occasional stirring. The hydrated carrier was then decanted with the distilled water and transferred into a glass column with an inner diameter of 15 mm where it formed a bed with a height of 145 mm.

Lactic acid producing bacteria (*Lactobacillus amylovorus*, NRRL B-4540) were cultured in a liquor (DIFCO 0881-01-3) for 48 hours at 30° C. 50 ml of the cell suspension were pumped through the carrier bed at a flow velocity of 25 ml/h. Subsequently, a further 50 ml of distilled water were pumped through. The outflow of the column was collected until it was clear, the total volume amounting to 75 ml. After use, the bioreactor was prepared for reuse by sterilisation and reloading as follows.

The bioreactor was sterilised by the passage of approximately 5 bed volumes of 2% NaOH at 73° C. until the colour of the outflow was low. The bioreactor was rinsed by the passage of sterile water at 73° C. and at a flow rate of about 2 bed volumes/h until the pH of the outflow was 10.8. The rinse water was replaced with a 0.5% solution of citric acid at 22° C. which was passed through the bioreactor at 2 bed volumes/h until the pH of the outflow was 4.2. The acid solution was replaced by sterile water at.30° C. which was passed through the column at 2 bed volumes/h.

*Pediococcus pentosaceus* (VTTE-88317) which had been cultured in wort with no hops or hop extracts for 48 hours at 30° C. was then immobilised in the bioreactor. 50 ml of the cell suspension were pumped through the carrier bed at a flow velocity of 25 ml/h and, subsequently, a further 50 ml of distilled water were pumped through. The outflow of the column was collected until it was clear, the total volume amounting to 75 ml. The loading of cells in the bioreactor was $3.96 \times 10^9$ CFU/g dry carrier.

EXAMPLE 3

Treatment of wort

Wort produced in the usual manner but which did not contain hops or hops extract was placed in the bioreactor produced in example 2. The sugar content of the wort amounted in this case to 15.1% with respect to the refractometric Brix-scale and the pH-value was about 5.50. The wort was fed at a temperature of 48° C., a pressure of 1 bar and a contacting time of 10 minutes through the reactor. The pH-value of the outflow was about 3.5.

EXAMPLE 4

Production of L(+) lactic acid

A jacketed 1.5 cm id. glass reactor was packed with 10 g Spezyme GDC 220, a commercial product produced essentially according to EXAMPLE 1, in sterile distilled water at 30° C. The packed volume of the bed was approx. 25–30 ml. 50 ml of a culture of Lactobacillus casei subsp. casei (ATCC 393, a known producer of diacetyl, culture CFU: $6.2 \times 10^9$ ml) grown in MRS Broth (Difco) was pumped into the reactor from top to bottom at a flow rate of 15 ml/h (approx. 0.5 bed volume/h) and the bacteria were immobilised by a single pass through the GDC bed. The number of cells immobilised in the reactor was quantified by suitable dilution and CFU counting on MRS Agar plates of the unbound cells. The biomass loading in the reactor was $2.7 \times 10^{11}$ CFU, equivalent to $8.9 \times 10^9$ CFU/ml of packed bed. A sterile feed solution consisting of glucose, 20 g/l; $MgSO_4.7H_2O$, 0.1 g/l; $MnSO_4.H_2O$, 0.05 g/l, $Na_2HPO_4$, 2 g/l and yeast extract (Difco), 1 g/l; pH 6.5 was then passed through the column at the same flowrate. Samples of the product effluent were collected daily for analysis of products. The samples were collected on ice to avoid any reactions during the collection period caused by the small number of viable cells which were continually removed from the column due to growth and/or leaching. Production of acid in the reactor was conveniently monitored by measuring the pH of the outflow which was typically about 2 pH units below that of the feedstream.

The reactor was maintained in operation for 6 days, during which the concentration of L(+) lactic acid (determined by an enzyme test kit - Boehringer Mannheim Cat. No. 139 084) in the outflow rose from 0.36 g/l on day 1 (flow rate 15.6 ml/h) to 0.43 g/l on day 6 (flow rate 12.4 ml/h). D(−) lactic acid was at or below the detection limit of the method (0.02 g/l) throughout.

The production rate of L(+) lactic acid was thus 187 mg/l.h (2.08 mg/h/$10^{11}$ CFU) on day 1 and 178 mg/l.h (1.97 mg/h/$10^{11}$ CFU) on day 6.

An otherwise identical reactor having a lower loading of $4.1 \times 10^{10}$ CFU produced L(+) lactic acid at a similar space-time yield (264 mg/l.h) but at a significantly higher yield based on biomass (19.4 mg/h/$10^{11}$ CFU).

ii) A reactor utilising Lactococcus lactis subsp. lactis (LMG 6890), a known homofermentative lactic acid bacterium producing L(+) lactic acid was set up and run as described in EXAMPLE 4 i) at a loading of $9.2 \times 10^{10}$ CFU. Over a period of 7 days operation, the concentration of L(+) lactic acid in the outflow was 1.3–1.5 g/l; D(−) lactic acid was at or below the level of detection. The space-time productivity was 667 mg/l.h and the productivity based on biomass was 21.8 mg/h/$10^{11}$ CFU. An important characteristic of this microbial strain for use in immobilised reactors as described herein which will be apparent to those skilled in the art is the low number of cells present in the outflow (50–500 CFU/ml).

iii) A reactor utilising a different strain of Lactococcus lactis subsp. lactis (LMG 7930), a known producer of nisin, was set up as described in Example 4 i) at a loading of $1.25 \times 10^{11}$ CFU. The reactor was run essentially as described on a sterile feed solution containing glucose, 20 g/l; trisodium citrate, 2 g/l; yeast extract, 1 g/l; bacteriological peptone, 5 g/l; $MgSO_4.7H_2O$, 0.2 g/l; $K_2HPO_4$, 5 g/l; $Na_2SO_4$, 1 g/l; pH 6.7. Over 6 days of operation, the concentration of L(+) lactic acid in the outflow was 2.9–3.1 g/l; D(−) lactic acid was at or below the level of detection. The space-time productivity was 1653.3 mg/l.h and the productivity based on biomass was 39.7 mg/h/$10^{11}$ CFU.

EXAMPLE 5

Additional production of diacetyl i) The reactor described in Example 4 i) produced a range of flavour compounds typical of lactic acid bacteria in addition to L(+) lactic acid. The flavour compounds were analysed by headspace GLC-MS as described by A. Kaipainen, Journal of High Resolution Chromatography 15 751–755 (1992)o This method provides a suitable low level of detection but quantitation by comparison with authentic standards is not as accurate as other methods such as GLC with FID detection. The Lactobacillus casei subsp. casei ATCC 393 used in the reactor described in Example 4 i) produced diacetyl at approx. 1000 ppm at early times during its operation, although the production of diacetyl declined with time while the production of L(+) lactic acid remained constant. At early time of operation, the space-time productivity of the reactor was 520 mg diacetyl/l.h and expressed on a biomass basis it was 5.8 mg/h/$10^{11}$ CFU.

EXAMPLE 6

Additional production of nisin i) The reactor described in Example 4 iii) produced nisin in addition to L(+) lactic acid. Nisin was detected and assayed by a growth inhibition test using a sensitive indicator strain of Micrococcus flavus (NCIB 8166) in a microtitre plate assay similar to that described by Nissen-Meyer et al. Journal of General Microbiology (1993) 139 1973–1978. Serial dilutions of the product from the reactor were made in the microtitre plate wells with an inoculum of the test organism in MRS Broth. The growth of the test organism was followed in a Bioscreen instrument which monitored total growth in the wells. The reactor product dilution that gave a 50% inhibition of growth (as measured by the integral of turbidity and time, rather than the turbidity alone as used by Nissen-Meyer et al.) compared with a control containing the same concentration of lactic acid (3 g/l) and at the same pH as the reactor product (pH 4.5) was taken as the amount of reactor product that contained 1 BU (Bacteriocin Unit). The reactor product contained 300 BU/ml. The productivity of bacteriocin (taken to be nisin on the basis of the producing organism and the sensitivity of the indicator strain) was $160 \times 10^3$ BU/l.h and 3840 BU/h/$10^{11}$ CFU.

EXAMPLE 7

Additional production of enzymes

A sample of the outflow on day 2 of operation from the reactor containing immobilised Lactococcus lactis subsp. lactis (LMG 7930, Example 4 iii)) was first filtered through a 0.2 μm filter to remove any bacterial cells and then concentrated 5-fold by passage through an ultrafiltration membrane of 10000 NMWL (Millipore Ultrafree—CL). A standard protease assay of the concentrate at pH 4 involving the hydrolysis of casein substrate failed to detect the presence of protease enzyme activity. However, lipase activity could be detected in the same concentrated sample in a standard pH-stat assay involving the hydrolysis of olive oil in a 5% w/v emulsion in gum arabic (2% w/v) with $CaCl_2$ (0.51% w/v) at 40° C. and pH maintained at 8 by titration with 0.01 M NaOH. 1 U of lipase activity is defined as the rate of release of 1 μmole of fatty acid per minute (equal to the rate of titration of NaOH in μmole/min) under these conditions. The lipase activity was 0.022 U/ml in the reactor outflow and the productivity of the reactor was 11.9 lipase U/l.h or 9.5 lipase U/h/$10^{11}$ CFU.

EXAMPLE 8

Production of DL lactic acid and other organic acids i) It is recognised that some lactic acid bacteria have homofermentative metabolism, giving rise to L(+) lactic acid, while others have heterofermentative metabolism, giving rise to both L(+) and D(-) lactic acids and other organic acids such as acetic acid. In addition, some lactic acid bacteria have a racemase enzyme which can interconvert L(+) and D(-) lactic acids. A mixture of L(+) and D(-) lactic acids were produced by a reactor containing immobilised *Leuconostoc mesenteroides* subsp. *mesenteroides* (DSM 20187) set up and operated as follows. The organism was grown in shake flask culture on MRS Broth and immobilised as described in Example 4 i). The loading of cells in the reactor at the start was $3.2 \times 10^{10}$ CFU. The reactor was run at 27° C. with a feed containing sucrose, 20 g/l; $MgSO_4.7H_2O$, 0.1 g/l; $MnSO_4.H_2O$, 0.05 g/l; $Na_2HPO_4$, 2 g/l; yeast extract, 1 g/l; pH 6.5 at a nominal flow rate of 15 ml/h. Acid production was evident by acidification of the feed as it passed through the reactor, the pH of the outflow being 3.8 after 6 days of operation. On day 6, the concentration of D(-) lactic acid in the outflow was 0.7 g/l and that of L(+) lactic acid was 0.1 g/l. The productivity of the combined DL lactic acid was 381 mg/l. h (35.8 mg/h/$10^{11}$ CFU based on the originally applied cells). One characteristic of this organism under the operating conditions was a significant growth of biomass in the reactor during operation but the maintenance of an acceptably low level of biomass in the outflow (about $3 \times 10^4$ CFU/ml). Acetic acid was not detected in this reactor loaded with *Leuconostoc mesenteroides* subsp. *mesenteroides* (DSM 20187).

ii) In a reactor loaded with *Lactococcus lactis* subsp. *lactis* (LMG 7930) (Example 4 iii)) a low concentration of acetic acid was detected above the detection limit of 0.05 g/l in the HPLC assay employed. In addition to the L(+) lactic acid and nisin produced in this reactor, acetic acid at 0.06 g/l was found in the outflow early in the operation of the reactor.

EXAMPLE 9

Additional Production of Dextrans i) The reactor containing *Leuconostoc mesenteroides* subsp. *mesenteroides*, a known producer of dextrans, described in Example 8 i) produced dextrans in addition to lactic and acetic acids. The presence of dextrans in the reactor outflow could not be shown by measuring the viscosity of the outflow but could be shown by precipitating the dextrans using alcohol, hydrolysing the dextrans using a specific enzyme and measuring the glucose released by the standard DNS assay for reducing sugars as follows. A sample of the reactor outflow, either 30 or 50 ml, was treated by the addition of 5 M sodium acetate (1 ml/10 ml sample) and isopropanol (final concentration, 67%) at room temperature to precipitate the dextrans which were recovered by centrifugation. The supernatant was discarded and the dextran pellet washed substantially free of other components, particularly sugars, by redissolving in distilled water by incubation in a boiling water bath for 10 min and re-precipitating with alcohol as above. The final pellet was dissolved in 1 ml of distilled water by boiling and 1 ml of 0.1 M sodium acetate buffer, pH 5.3 was added. 1 ml of this solution was incubated with 1 μl of a dextranase enzyme preparation (Amano) for 1 h at 50° C. to hydrolyse the dextran. The reaction was terminated by the addition of 4 ml of DNS reagent (1% 3,5-dinitrosalicylic acid, 1.6% sodium hydroxide and 30% K—Na tartrate) and the mixture placed in a boiling water bath for 6 min. The glucose concentration was measured by comparing the absorbance at 540 nm of the sample with a standard curve prepared with the same batch of DNS reagent and known glucose concentrations. The observed values were corrected for the absorbance of a control assay performed on the other 1 ml of dextran solution in the same way with the exception that the dextranase was added after the DNS reagent. The concentration of dextran in the reactor outflow was 0.04 g/l on day 6 of operation. The productivity of the reactor was 19.1 mg dextran/l.h and 1.79 mg dextran/h/$10^{11}$ CFU.

ii) The reactor described in Example 9 i) was constructed and run in such a way that the effluent from the packed bed was collected as the reactor outflow directly after it had passed through the bed. Since dextran synthesis is known to be the result of the action of a free, extracellular enzyme, dextransucrase, on the sucrose in the feed, greater production of dextran might be achieved by allowing a longer time for the dextransucrase reaction to occur under the near ideal conditions in the reactor. Another reactor was constructed with a similar bed of immobilised *Leuconostoc mesenteroides* subsp. *mesenteroides* (DSM 20187) placed at the bottom of a glass jacketed reactor. The reactor was run by passing the feed from bottom to top so that the outflow from the packed bed remained in the space above the bed for about 6.4 h before passing out of the reactor to be collected on ice. The reactor was set up essentially as described in Examples 4 i) and 8 i) with a loading of cells of $1 \times 10^{10}$ CFU. The feed was the same as described in Example 8 i) at a nominal flow rate of 13 ml/h (about 0.5 bed volumes/h). Dextran concentration in the reactor outflow as measured by the analysis described above was constant between days 5 and 8 of operation at 0.09 g/l. The reactor productivity was 39 mg dextran/l.h and 11.7 mg dextran/h/$10^{11}$ CFU.

EXAMPLE 10

Urea removal/degradation during passage through the reactor

A reactor constructed essentially according to Example 4 i) with *Lactobacillus fermentum* (ATCC 9338) at a loading of $1.12 \times 10^{10}$ CFU was operated with a feed containing nominally glucose, 20 g/l; urea 4 g/l; $MgSO_4.7H_2O$, 0.1 g/l; $MnSO_4.H_2O$, 0.05 g/l; $Na_2HPO_4$, 2 g/l; yeast extract, 1 g/l; pH 6.5. After autoclaving the feed, the urea concentration was 2.7% as determined by HPLC analysis on a $Ca^{2+}$ ion exchange column at 85° C. using $Ca(NO_3)_2$ solution as isocratic eluent. The feed was passed through the reactor at 21.0 ml/h and the concentration of urea in the outflow was determined by HPLC as above. The urea concentration in the outflow was lowered by 0.3 g/l. The urea removal rate was 310 mg/l.h and 56 mg/h/$10^{11}$ CFU.

We claim:

1. A bioreactor having immobilized, lactic acid bacteria, comprising a substantially non-compressible carrier and lactic acid bacteria immobilized on a surface of said carrier, wherein said carrier comprises a continuous, porous matrix or dimpled or reticular porous particles, wherein the matrix or the particles have a structure of a loosely associated plurality of microparticles or microfibers which are bound together chemically, adhesively or mechanically at least at some contact points between individual microparticles or microfibers and wherein the microparticles or microfibers comprise a material with anion exchanger capability.

2. The bioreactor of claim 2, wherein said material is a resin.

3. The bioreactor of claim 1, wherein the carrier comprises cellulose or rayon or their derivatives.

4. The bioreactor of claim 3, wherein the carrier is diethylaminoethylene-modified cellulose (DEAE cellulose), and wherein the microparticles or microfibers are agglomerated with polystyrene.

5. The bioreactor of claim 1, wherein the loading capacity (number of bacteria cells/g dry carrier) is $10^8$ to $10^{12}$.

6. The bioreactor of claim 1, further comprising a device allowing contact of the carrier with a fluid to be reacted.

7. The bioreactor of claim 6, wherein the device is selected from the group consisting of a stirred tank reactor, basket reactor, fluidized bed reactor, packed bed reactor and filter reactor.

8. The bioreactor of claim 6, wherein the device represents a column or a plurality of columns.

9. The bioreactor of claims 6, 7 or 8, further comprising a container for hydration of the carrier before pumping fluid into the bioreactor, a container with sterilizing liquid to sterilize the carrier in the bioreactor, a container with neutralization liquid to neutralize the carrier after sterilizing, a container with bacteria suspension for pumping into the bioreactor and for fixing the bacteria on the surface of the carrier, a container with a substrate to be treated, optionally a post-treatment container in which outflow from the bioreactor is collected, and a container for storage of reaction product.

10. The bioreactor of claim 8, wherein the plurality of columns are in parallel.

11. The bioreactor of claim 1 further comprising pressure outlet valves, means for separating carbon dioxide, or both.

12. A method of making a lactic acid bacteria-metabolized product, comprising the steps of reacting a starting material with the bioreactor of claim 1 so that the starting material is metabolized by the lactic acid bacterial, and obtaining the lactic acid bacteria-metabolized product.

13. The method of claim 12, wherein the product is lactic acid.

14. The method of claim 13, wherein the starting material is food or feed product.

15. The method of claims 12 or 14, wherein said product is an acidified beverage.

16. The method of claim 13, wherein said lactic acid is L(+) lactic acid.

17. The method of claim 12, wherein the product is a flavour compound.

18. The method of claim 12, wherein said product is a bacteriocin.

19. The method of claim 12, wherein said product is an organic acid other than lactic acid.

20. The method of claim 12, wherein said product is an extracellular enzyme.

21. The method of claim 12, wherein said product is a polymer obtainable with lactic acid bacteria.

22. The method of claim 12, wherein said product is urea.

* * * * *

UNITED STATES PATENT AND TRADEMARK OFFICE
CERTIFICATE OF CORRECTION

PATENT No.       :   5,635,368

DATED            :   June 3, 1997

INVENTOR(S)      :   Heikki LOMMI et al.

It is certified that error appears in the above-identified patent and that said Letters Patent is hereby corrected as shown below:

Column 2, line 59, "$10_8$ to $10_{12}$" should be --$10^8$ to $10^{12}$--.

Column 4, line 31, "Of" should be --of--.

Column 6, line 24, "(1992)o" should be --(1992).--.

Column 7, line 48, "3 x 104" should be --3 x $10^4$--.

Column 8, line 49, no new paragraph should begin, it is a continuation of line 48.

Column 8, line 55, no new paragraph should begin, it is a continuation of line 54.

Column 9, line 17, after "microfibers" insert --,--.

Column 9, line 19, "claim 2" should be --claim 1--.

Signed and Sealed this

Second Day of December, 1997

*Attest:*

BRUCE LEHMAN

*Attesting Officer*      *Commissioner of Patents and Trademarks*